United States Patent [19]

Poddevin et al.

[11] Patent Number: 6,120,558

[45] Date of Patent: Sep. 19, 2000

[54] METHOD FOR MANUFACTURING AND TREATING TEXTILES

[75] Inventors: Nicolas Poddevin, Colomiers; Jacques Fages, Albi; Robert Guidoin, Bauge, all of France

[73] Assignee: Bioland, Toulouse, France

[21] Appl. No.: 09/202,688

[22] PCT Filed: Jun. 17, 1997

[86] PCT No.: PCT/FR97/01093

§ 371 Date: Dec. 18, 1998

§ 102(e) Date: Dec. 18, 1998

[87] PCT Pub. No.: WO97/48848

PCT Pub. Date: Dec. 24, 1997

[30] Foreign Application Priority Data

Jun. 18, 1996 [FR] France ................................ 96 07720

[51] Int. Cl.$^7$ .......................... D06F 19/00; D03D 15/00; D04H 13/00

[52] U.S. Cl. ................ 8/137.5; 8/137; 442/301; 442/414

[58] Field of Search .......................... 8/137, 137.5, 474, 8/475; 442/301, 414; 428/913

[56] References Cited

U.S. PATENT DOCUMENTS

| | | |
|---|---|---|
| 4,012,194 | 3/1977 | Maffei . |
| 4,563,489 | 1/1986 | Urist .......................................... 524/21 |
| 4,749,522 | 6/1988 | Kamarei . |
| 4,997,446 | 3/1991 | Thoma ........................................ 623/16 |
| 5,010,145 | 4/1991 | Ikada et al. .............................. 525/415 |
| 5,206,341 | 4/1993 | Ibay et al. ................................ 528/361 |
| 5,593,778 | 1/1997 | Kondo et al. ............................ 428/373 |
| 5,766,618 | 6/1998 | Laurencin et al. ...................... 424/426 |
| 5,833,641 | 11/1998 | Curtic et al. .............................. 602/43 |
| 5,833,891 | 11/1998 | Subramaniam et al. .................... 264/7 |
| 5,985,776 | 11/1999 | Bertrand et al. ........................ 442/400 |

FOREIGN PATENT DOCUMENTS

| | | |
|---|---|---|
| 0 464 163 | 1/1992 | European Pat. Off. . |
| 0 518 653 | 12/1992 | European Pat. Off. . |
| 0 530 949 | 3/1993 | European Pat. Off. . |
| 0 679 753 | 11/1995 | European Pat. Off. . |

OTHER PUBLICATIONS by J.W. Tom et al., "Formation of Bioerodible Polymeric Microspheres and Microparticles by Rapid Expansion of Supercritical Solutions", *Biotechnol. Prog.* 1991, vol. 7, No. 5, pp. 403–411.

*Primary Examiner*—Yogendra Gupta
*Assistant Examiner*—Christine Ingersoll
*Attorney, Agent, or Firm*—Young & Thompson

[57] ABSTRACT

A method for treating after its manufacture a textile structure containing at least one polymer of the poly ($\alpha$-hydroxy-acids) family obtained by at least one step of mechanical assembly of textile fibers. The structure is contacted with a flow of a composition of at least one fluid in supercritical state. The invention also concerns a method for manufacturing a structure and the resulting structure.

20 Claims, No Drawings

METHOD FOR MANUFACTURING AND TREATING TEXTILES

CROSS REFERENCE TO RELATED APPLICATION

This it the 35 USC 371 National Stage of International application PCT/FR97/01093 filed on Jun. 17, 1997, which designated the United States of America.

FIELD OF THE INVENTION;

The invention concerns the manufacture and treatment of a textile structure containing at least one polymer of the poly($\alpha$-hydroxy-acids) family, i.e. comprising textile fibres incorporating a portion of at least one polymer of the poly($\alpha$-hydroxy-acids) family.

In all the present application, the expression "textile structure" covers not only all textile structures obtained by assembling threads or spun yarns of fibres (woven, non-woven, braided, knitted, tulle, composite etc.), in the cut-up state or in a sheet or even in a reel, but also threads, spun yarns, filaments, cords, cables themselves, also designated hereinafter in a generic manner by the term "threads".

BACKGROUND OF THE INVENTION.

In the textile industry, textile fibres are assembled mechanically during at least one mechanical assembly stage such as spinning (all the operations for assembling fibres together in order to obtain a thread); braiding, knitting and weaving (assembling threads by interlacing and/or looping together etc.); felting, adhesive bonding, agglomeration of fibres and/or threads and/or several materials to each other or to other products (non-woven, composite etc.)

After these assembly stages, the so-called "loomstate" or gray pieces, undergo finishing treatments (desizing, bleaching, dyeing, printing, application of finishes, etc.).

At the end of all these stages, the textile structure obtained has the desired forms and appearance, but it incorporates many undesirable and useless impurities, trapped within the structure, and which do not enter into the composition of the fibres or the structure. Among these impurities reference may be made to: impurities incorporated in the fibres when the fibres themselves are obtained or manufactured; additives and impurities deliberately incorporated or not (for example oiling or antistatic additives) during the assembly stages; organic contaminants or microorganisms etc.

Taking into account the great difficulty of eliminating all these impurities incorporated within the structure itself and the fibres, one is resigned in most applications to use these textile structures contaminated in this way.

In the particular case where purification is essential, for example for the manufacture of implantable materials having a textile fibre structure (artificial ligaments, adhesive dressings, artificial membranes, vascular prostheses etc) a succession of multiple complex stages are carried out having very different natures(suitable for eliminating each type of impurity) which are sophisticated : washing, cleaning desizing, disinfecting, elimination of solvents, neutralization etc.

All these treatments consist of using active products such as detergents, disinfectants and harmful powerful solvents which may themselves remain as traces in the structure and are dangerous for operators. Moreover, these treatments are long, costly and often polluting as a result of the use of these powerful and harmful products.

In spite of all these treatments, it is not a rare occurrence to find that the structures remain somewhat contaminated. For example, it has been demonstrated that negative immune reactions may be due to these types of contamination on the surface of vascular prosthesis implanted under perfectly sterile conditions.

Such is in particular the case with structures of bioresorbable textile fibres made of sensitive polymers which do not withstand solvents, detergents or disinfectants, or heat treatments. The use of these fibres for the manufacture of parts requiring great purity has therefore hitherto been rejected.

Now, these delicate textile fibres sometimes possess, moreover, particular properties which are desired for precise applications. Such is the case in particular of fibres containing at least one poly($\alpha$-hydroxy-acid) which are biocompatible and/or biodegradeable, and in particular fibres of polyglycollic acid (PGA) which have excellent bioresorption properties.

Nevertheless, it was hitherto considered that polymers of the poly($\alpha$-hydroxy-acids) family could not be subjected to intense physico-chemical treatments, taking into account their great fragility. In particular, it is known that polymers of the poly($\alpha$-hydroxy-acids) family are soluble in fluids in the supercritical state (cf. for example "Formation of bioredible polymeric microspheres and microparticles by rapid expansion of supercritical solutions", J. W. Tom and P. G. Debenedetti, Biotechnol. Prog., 1991, 7, 403-411; EP-0 464 163 etc). Moreover purification treatments applied to these materials have the consequence of making them fragile, even though these treatments always remain imperfect. Thus for many applications, the need has been apparent for a treatment process enabling textile structures based on polymers of the poly($\alpha$-hydroxy-acids) family to be completely purified and which does not degrade the mechanical properties of the structure.

SUMMARY OF THE INVENTION

Now, the inventors have surprisingly found, in contradiction to the prior teachings, that a textile structure containing at least one polymer of the poly($\alpha$-hydroxy-acids) family may be subjected to a treatment by a composition of a fluid or fluids in the supercritical state, without any damage to the structure. The inventors have also shown that this treatment then enables such a textile structure to be purified integrally and in a single stage, not only while preserving the physico-chemical integrity of the structure but even, in a still more surprising manner, while enhancing its mechanical properties.

To this end, the object of the invention is to provide a process for manufacturing and treating a textile structure containing at least one polymer of the poly($\alpha$-hydroxy-acids) family enabling a textile structure to be obtained that is pure and/or has reinforced mechanical properties.

The object of the invention is more particularly to provide. a simple, low cost, efficient treatment for purifying textile structures containing at least one polymer of the poly($\alpha$-hydroxy-acids) family by eliminating various undesirable physico-chemical compounds and, simultaneously, eliminating various organic contaminants and biochemical contaminants (micro-organisms), while preserving the physico-chemical integrity of the structure.

Accordingly, the object of the invention is to provide a treatment process for the total purification in a single stage of textile structures containing at least one polymer of the poly($\alpha$-hydroxy-acids) family.

The object of the invention is also in particular to provide a treatment for textile structures containing at least one polymer of the poly($\alpha$-hydroxy-acids) family enabling the mechanical strength of these structures to be reinforced.

The poly(α-hydroxy-acids) family comprises polymers having the general formula:

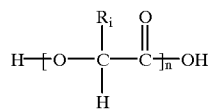

where $R_1$ is hydrogen or methyl. This family not only comprises homopolymers agreeing with this formula, but also corresponding copolymers and mixtures of these polymers and copolymers. Among these polymers, reference may be made to polyglycollic acid (PGA) and polylactic acids (L-PLA, D-PLA, DL-PLA) and poly(lactide-coglycollite) copolymers (PLA/GA).

All these polymers have similar properties. In particular, they are biocompatible and biodegradable. For example, a PGA implant is bioresorbable within a period of 1 to 6 months. In addition, above a certain value of the molecular weight which depends on each polymer or on each polymeric composition, they may be spun by extrusion and enable textile structures to be produced.

The object of the invention is also to provide such a process which enables textile structures to be obtained containing in particular biodegradable or bioresorbable structures which can enter into the composition of implants (implantable parts) for man or animals.

Accordingly, the object of the invention is to provide in particular a process for treating textile structures before implantation—in particular threads or a woven and/or knitted and/or braided and/or agglomerated (non-woven, composite) structure etc, containing at least one polymer of the poly(α-hydroxy-acids) family, which guarantees the purity and sterility of these structures, while preserving their physico-chemical and mechanical integrity.

The object of the invention is also to provide a treatment process which does not involve heating the parts to a high temperature, and which can thus be employed at a low temperature (in particular below 60° C.).

The object of the invention is also to provide a treatment process which is extremely clean, producing no polluting or toxic effluents and which is not dangerous for operators.

The object of the invention is also to provide such a process which increases the possibilities of using textile fibres containing at least one polymer of the poly(α-hydroxy-acids) family, in particular in order to obtain bioresorbable materials or parts that are implantable in the human body or in animal bodies.

To this end, the invention concerns a process for treating a textile structure, after its manufacture, containing at least one polymer of the poly(α-hydroxy-acids) family obtained by at least one mechanical stage (spinning and/or braiding and/or knitting and/or weaving and/or agglomerating etc.) for assembling textile fibres at least partially formed of fibres containing a proportion of at least one polymer of the poly(α-hydroxy-acids) family of which the molecular weight is adapted so as to enable the said structure to be obtained, wherein the structure is subjected to at least one treatment stage (in particular one and only one stage) during which it is put into contact with a flow of a composition of at least one fluid in the supercritical state.

Advantageously and according to the invention, the composition and the duration of the treatment stage are chosen so as to eliminate impurities trapped within the structure in order to enable it to be subsequently implanted in the human body or an animal body, and so as at least to preserve the integrity of the structure.

The molecular weight of poly(α-hydroxy-acids) polymers entering into the composition of the fibres enabling the structure to be obtained is adapted (in particular sufficiently) to permit the fibres to be assembled (in particular by spinning through hot extrusion). In point of fact, in particular, spinning by hot extrusion of fibres of these polymers is only possible with a satisfactory quality above a certain value for the molecular weight which depends on the exact chemical composition of the polymers and of the assembly process used.

In the case of PGA, the molecular weight of the polymer must usually be greater than 30,000, in particular of the order of 120,000, for spinning by hot extrusion of threads intended for weaving.

It will be recalled that fluids in the supercritical state may be defined as gases placed under conditions of temperature and pressure such that their properties are intermediate between those of gases and those of liquids. They are also referred to as "dense gases" or "expanded liquids". For a given chemical body, the precise point of the temperature-pressure diagram for which the two liquid and vapour phases combine to form one phase is called the critical point. Beyond this critical temperature (Tc) and this critical pressure (Pc) the fluid is in a so-called "supercritical" state.

Different fluids in the supercritical state may be used within the context of the invention. It should be noted in this respect that although supercritical fluids are especially known for their ability to abstract organic materials from vegetables or organs (for example U.S. Pat. No. 4,749,522) the invention has demonstrated that these fluids enable textile structures containing at least one polymer of the poly((α-hydroxy-acids) family to be simultaneously washed, cleaned, desized and disinfected with very great efficiency, while having, surprisingly, a high degree of physico-chemical and mechanical neutrality towards this structure and polymers of the poly(α-hydroxy-acids) family and even reinforcing the mechanical strength of the structure.

Advantageously and according to the invention, carbon dioxide in the supercritical state is chosen as the composition of the fluid(s) in the supercritical state.

Advantageously and according to the invention, the part is placed in contact with a flow of supercritical carbon dioxide for a period of between 1 h and 24 h, in particular of the order of 12 h.

The invention also extends to a process for manufacturing a textile structure containing at least one polymer of the poly(α-hydroxy-acids) family, wherein the structure is produced by at least one mechanical stage (spinning and/or braiding and/or knitting and/or weaving and/or agglomerating) for assembling textile fibres at least partially formed of fibres containing a proportion of at last one polymer of the poly(α-hydroxy-acids) family of which the molecular weight is adapted so as to enable the said structure to be obtained, wherein, after having carried out all the assembly stages enabling the structure to be obtained, the structure is subjected to at least one treatment stage (in particular one and only one stage) during which it is placed in contact with a flow of a composition of at least one fluid in the supercritical state.

Advantageously, and according to the invention, the composition and the duration of the treatment stage are chosen so as to eliminate the impurities trapped within the structure so that it can be subsequently implanted in the human body or an animal body, and so as at least to preserve the physical integrity of the structure.

Advantageously and according to the invention, the structure is produced by assembling threads obtained by extrusion of fibres containing at least one polymer of the poly (α-hydroxy-acids) family.

According to the invention, the textile structure contains at least a substantial proportion (in particular more than 1%) of poly(α-hydroxy-acids). In other words, the textile structure comprises fibres containing a substantial proportion of at least one polymer of the poly(α-hydroxy-acids) family of which the molecular weight is adapted so as to allow the structure to be obtained.

The invention is applicable whatever the proportion of polymers of the poly(α-hydroxy-acids) family, in particular fibres of this polymer or these polymers, contained in the textile structure. Nevertheless, advantageously and according to the invention, the structure is produced with threads obtained by extruding fibres of poly(α-hydroxy-acid(s)) —in particular PGA —, i.e. the structure is formed with a 100% fibres comprising 100% poly(α-hydroxy-acid(s) —in particular PGA.

Advantageously, in a manufacturing process according to the invention, the final packaging of the structure is carried out after the treatment stage.

Advantageously and according to the invention, the structure is subjected to one and only one treatment stage after all the assembly stages enabling the structure to be obtained. Advantageously and according to the invention, the part is preferably subjected to the treatment process immediately after having carried out all the assembly and finishing stages in order to obtain the structure, and on the same site. Thus, advantageously and according to the invention, the treatment stage is carried out immediately after the part is manufactured.

The invention also extends to a bioresorbable textile structure containing at least one polymer of the poly(α-hydroxy-acids) family obtained by at least one mechanical stage (spinning and/or braiding and/or knitting and/or weaving and/or agglomerating etc.) for assembling textile fibres at least partially formed of fibres containing a proportion of at least one polymer of the poly(α-hydroxy-acids) family of which the molecular weight is adapted so as to enable the structure to be obtained, and having been obtained by a process according to the invention. Advantageously and according to the invention, the structure is formed of an assembly of threads obtained by extruding fibres containing (in particular consisting of) at least one polymer of the poly(α-hydroxy-acids) family of which the molecular weight is adapted so as to enable the structure to be obtained, in particular a woven and/or knitted and/or braided and/or agglomerated assembly of threads. Advantageously and according to the invention, the structure is formed of a bioresorbable piece woven from PGA threads. A textile structure according to the invention is free from impurities and has, at the same time physico-chemical and mechanical properties which are unchanged or even reinforced. Such a structure could not hitherto be obtained in the prior art.

In particular, the invention accordingly concerns a sterile and pure piece comprising a textile structure of fibres containing at least one polymer of the poly(α-hydroxy-acids) family according to the invention which is sufficiently pure so as to be implantable in man or in an animal, including on particularly sensitive implantation sites. The mechanical and physico-chemical properties of the piece are similar to, or even improved, in comparison with those of an impure piece or one not treated in accordance with the invention.

The invention also extends to the application of a treatment process according to the invention for treating implants with a textile structure according to the invention, before they are implanted in the human body or in an animal body, in particular implants in the form of threads or implants with a woven and/or knitted and/or braided and/or agglomerated structure, containing at least one polymer of the bioresorbable poly(α-hydroxy-acids) family.

The invention also extends to the application of a manufacturing process according to the invention for manufacturing implants with a textile structure containing at least one polymer of the poly(α-hydroxy-acids) family.

The invention also concerns a treatment process, a manufacturing process, a structure and a part or implant, wherein it has all or part of the characteristics mentioned above or below, in combination.

DETAILED DESCRIPTION OF THE INVENTION

Other features and advantages of the invention will be apparent from the following examples.

EXAMPLE 1

A piece was produced with a woven textile structure having a satin weave with threads formed of fibres of polyglycollic acid (PGA 100) having a picks count of 25 threads/cm and an ends count of 85 threads/cm. It should be noted that these polyglycollic acid fibres are bioresorbable fibres and are particularly sensitive and fragile to conventional purification treatments.

A fragment of this piece was subjected to a treatment according to the invention, by placing it in contact with a flow of supercritical carbon dioxide at a pressure of $2.8 \times 10^7$ Pa for 15 hours at 35° C. with a mean flow rate of 54.6 kg/h of supercritical $CO_2$. It was found by visual examination and by touch that the piece had not been adversely affected from the point of view of its appearance, flexibility and strength.

Analysis for contamination was then carried out on the fragment of the piece thus treated. The total absence was noted of aerobic and mesophyllic micro-organisms, yeasts or moulds.

A sterility check carried out on the fragment of the piece demonstrated that it was sterile after treatment.

Mechanical breaking strength tensile tests were carried out on the fragment of the piece treated according to the invention, on a non-treated control fragment of the same piece and on a fragment of the same piece sterilized with γ rays and not treated with supercritical $CO_2$.

The results were as follows:

untreated control fragment:
  732 N–727.5 N–730 N, i.e. a mean value of 729.8 N,
fragment sterilized with γ rays:
  617.5 N–614 N–625 N, i.e. a mean value of 618.8 N,
fragment treated according to the invention:
  762 N–732.5 N–735 N, i.e a mean value of 743.1 N.

Thus, contrary to sterilization with γ rays, which reduced the strength of the textile structure by more than 15%, treatment according to the invention increased this strength by about 2%. This phenomenon found no clear explanation since PGA in the mass (raw undivided) is normally soluble in supercritical carbon dioxide and it would thus be expected that the mechanical strength would on the contrary be considerably degraded.

EXAMPLE 2

Two fragments of the piece of satin weave fabric were produced as indicated in example 1. The first was used in the impure loom state while the second was subjected to the treatment with supercritical $CO_2$ of example 1.

These two fragments were analyzed, as well as a raw PGA thread used to produce the woven piece, by scanning electron microscopy, by infrared spectroscopy, ESCA and DSC.

Scanning Electron Microscopy (SEM):

Examination of the surface of the impure PGA thread showed the presence of a few impurities and a few defects produced during manufacture and/or during handling. The presence of impurities in the form of balls was observed on the surface of the threads of the piece before treatment according to the invention, but in general a layer was observed which covered the surface of the threads. A few impurities were observed on the piece after treatment according to the invention but the layer of impurities covering the surface of the piece before treatment according to the invention was no longer found. The layer of impurities introduced during weaving was thus washed away during the treatment according to the invention by the supercritical carbon dioxide.

XPS Analysis (ESCA):

XPS analyses were performed only on fragments from the piece, the diameter and texture of the raw thread making analysis impossible. General view and high resolution analyses were performed on the two fragments. Table 1 below gives the atomic composition of the surface of these fragments.

TABLE 1

Atomic composition

| | ATOMIC PERCENTAGE (%) | | | | | | |
|---|---|---|---|---|---|---|---|
| | C | O | N | Si | Na | Cl | S |
| Fragment before treatment | 75.5 | 23.5 | — | 0.9 | — | 0.1 | — |
| Fragment after treatment | 69.5 | 29.7 | 0.2 | — | 0.3 | 0.1 | 0.2 |

These results show that the treatment of the invention brought about a modification of the atomic composition of the surface. In point of fact, a variation was produced in the proportion of C and O, as well as the disappearance of Si to the benefit of N, Na and S. Moreover, both fragments had a surface composition far removed from the theoretical composition of PGA (50% C and 50% O). This shows that the chemical composition of the surface of the fragments before treatment did not consist of pure PGA and that this chemical composition changed following treatment according to the invention.

High resolution analyses of the carbon (C1s) also revealed that the surface of the piece was modified by treatment according to the invention. Indeed, the following table 2 shows that the percentages of C—C and C—O bonds were reduced to the benefit of C=O bonds after treatment.

TABLE 2

Percentage chemical bonds of carbon

| | TYPE OF BOND (%) | | |
|---|---|---|---|
| | C—C | C—O | C=O |
| Fragment before treatment | 51.5 | 41.9 | 6.7 |
| Fragment after treatment | 47.5 | 38.2 | 14.32 |

FTIR Analysis:

The infrared spectra of the two fragments and of the raw thread were practically identical except as regards the characteristic bands of the $CH_2$ and $CH_3$ groups (between 2800 and 3100 $cm^{-1}$). It was found that the structure of the bands of three specimens was different and that the fragment before treatment had a different structure from that of the two other specimens. Indeed, two large peaks appeared at 2850 $cm^{-1}$ and 2920 $cm^{-1}$ after weaving and then disappeared after treatment according to the invention. The spectrum of the fragment after treatment differed very little from that of the raw thread.

DSC Analysis:

Table 3 below summarizes the results obtained from the thermograms.

TABLE 3

Results of DSC

| | Fusion temperatures ±1 (° C.) | Peak #1 ±1 (° C.) | Peak #2 ±1 (° C.) | ΔH of fusion ±4 (J/g) |
|---|---|---|---|---|
| PGA thread | 214 | 218 | 226 | 74 |
| Fragment before treatment | 215 | 218 | 225 | 82 |
| Fragment after treatment | 216 | 219 | 226 | 77 |

It should be noted that the values obtained for the fusion enthalpy are not significant, taking into account measurement uncertainties. As a consequence, these results confirm that the internal structure of the thread and fragments of the woven piece was not modified by the treatment of the invention.

It was thus found from all these analyses that:
- the treatment did not modify the intrinsic structure of second fragment and the PGA fibres,
- the two fragments enclosed contaminants of the hydrocarbon type which disappeared in the second fragment after the treatment according to the invention,
- the quality of cleaning the fibres after the treatment according to the invention was satisfactory,
- the treatment induced a modification in the chemical composition of the surface of the threads, which was probably responsible for an increase in the mechanical strength.

EXAMPLE 3

The viscosity of a fragment of a piece woven and treated according to the invention as described in example 1 was analyzed, comparing it with the viscosity of a raw PGA 100 thread and with that of a fragment of the same piece woven from PGA 100, not treated with supercritical carbon dioxide.

The viscosity is an indicator of the degradation of the textile structure of the woven piece. The higher the viscosity, the higher the molecular mass of the polymer and the less the textile structure of the woven piece is degraded.

An analysis of the viscosity gave the following results:

| Raw PGA thread: | 1.09 dl/g |
|---|---|
| Fragment before treatment: | 1.16 dl/g |
| Fragment after treatment according to the invention: | 1.13 dl/g |

These results show that the weaving stage in no way reduced the viscosity of the material, but that it was the same for the treatment according to the invention.

EXAMPLE 4

Threads of PGA 100 (100% polyglycollic acid) were treated with a flow of supercritical $CO_2$ for at least 12 hours at a temperature of 35° C. under a pressure of $2.7 \times 10^7$ to $2.8 \times 10^7$ Pa.

Several types of specimens were treated: single spun threads of raw PGA separated from each other and PGA threads compacted to form a non-woven structure.

At the end of this treatment with the supercritical fluid, all the specimens were compared with the same specimens before treatment with supercritical fluid. No difference in appearance, strength or flexibility was found from a visual examination and by touch.

Since the invention makes it possible simultaneously to purify textile structures containing at least one polymer of the poly(α-hydroxy-acids) family and reinforce their mechanical properties, it will find advantageous applications in all situations where one or other of these properties is sought. In particular, the woven PGA pieces treated according to the invention are pure and bioresorbable and can enter into the composition of implants or constitute implants for man or for animals (artificial ligaments, adhesive dressings, artificial membranes, vascular, cardiac or bone prostheses etc).

What is claimed is:

1. A process for treating a textile structure selected from the group consisting of threads, spun yarns, filaments, cords, cables and threads which may or may not have been assembled, said textile structure comprising at least one polymer of the poly (α-hydroxy-acids) family, said polymer having a molecular weight which is adaptable to obtain the textile structure; the process comprising:

subjecting the textile structure to at least one treatment stage during which structure is contacted with a flow of a composition of at least one fluid in the supercritical state; and wherein composition and the duration of the treatment stage are chosen so as to eliminate impurities trapped within the structure so that the structure can subsequently be implanted in a human body or an animal body, and the integrity of the structure is at least preserved.

2. The process according to claim 1, wherein the composition is carbon dioxide in the supercritical state.

3. The process according to claim 2, wherein the structure is contacted with a flow of supercritical carbon dioxide for a period of between 1 hour and 24 hours.

4. The process according to claim 3, wherein the structure is contacted with a flow of supercritical carbon dioxide for a period of about 12 hours.

5. A process for manufacturing a textile structure, which comprises:

producing the structure by at least one stage of mechanical assembly of textile fibers comprised at least partially of fibers containing a proportion of at least one polymer of the poly (α-hydroxy-acids) family, polymer having a molecular weight which is adaptable to produce the structure;

thereafter, after having carried out all stages of mechanical assembly to produce the structure, subjecting the structure to at least one treatment stage during which structure is contacted with a flow of a composition of at least one fluid in the supercritical state; and wherein composition and the duration of the treatment stage are chosen so as to eliminate impurities trapped within the structure so that the structure can subsequently be implanted in a human body or an animal body and the physical integrity of the structure is at least preserved.

6. The process according to claim 5, wherein the at least one stage of mechanical assembly is selected from the group consisting of spinning, braiding, knitting, weaving, agglomerating and combinations thereof.

7. The process according to claim 5, wherein the structure is produced by assembling threads obtained by extruding fibers containing at least one polymer of the poly (α-hydroxy-acids) family.

8. The process according to claim 5, wherein the structure is produced with threads obtained by extruding polyglycollic acid fibers.

9. The process according to claim 5, further comprising subjecting the structure to a final conditioning step after treatment stage.

10. The process according to claim 5, wherein the structure is subjected to one and only one purification stage after all stages of mechanical assembly.

11. The process according to claim 5, wherein the structure is subjected to the treatment stage immediately after having carried out all mechanical assembly and finishing stages.

12. The process according to claim 5, wherein the treatment stage is carried out immediately after the structure is produced.

13. The process according to claim 5, wherein the composition is carbon dioxide in the supercritical state.

14. The process according to claim 13, wherein the structure is contacted with a flow of supercritical carbon dioxide for a period of between 1 hour and 24 hours.

15. The process according to claim 14, wherein the structure is contacted with a flow of supercritical carbon dioxide for a period of about 12 hours.

16. A bioresorbable textile structure selected from the group consisting of threads, spun yarns, filaments, cords, cables and threads which may or may not have been assembled, said textile structure is obtained by at least one stage of mechanical assembly of textile fibers comprised at least partially of fibers containing a proportion of at least one polymer of the poly (α-hydroxy-acids) family, polymer having a molecular weight which is adaptable to obtain structure, and structure a) having been obtained by a process as claimed in claim 5, b) having been purified so as to substantially remove any impurities previ-ously incorporated in the structure during its mechanical assembly, and c) having its integrity at least preserved when compared to the initial structure before purification.

17. The structure according to claim 16, wherein structure is formed of an assembly of threads obtained by extruding fibers containing at least one polymer of the poly (α-hydroxy-acids) family.

18. The structure according to claim 16, wherein structure is formed of threads obtained by extruding polyglycollic acid fibers.

19. The structure according to claim 16, wherein structure is formed of a bioresorbable woven piece made of polyglycollic acid threads.

20. A sterile and pure piece comprising a textile structure of fibers containing at least one polymer of the poly (α-hydroxy-acids) family according to claim 16, wherein piece is sufficiently pure so as to be implantable in a human or animal body, and having its mechanical and physico-chemical properties at least preserved when compared with those of an impure piece obtained after mechanical assembly and before purification.

\* \* \* \* \*